(12) United States Patent
Yoshida et al.

(10) Patent No.: US 12,343,107 B2
(45) Date of Patent: Jul. 1, 2025

(54) BIOLOGICAL INFORMATION MEASUREMENT DEVICE

(71) Applicant: OMRON HEALTHCARE CO., LTD., Muko (JP)

(72) Inventors: Hideaki Yoshida, Kyoto (JP); Shinya Tanaka, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 835 days.

(21) Appl. No.: 16/774,313

(22) Filed: Jan. 28, 2020

(65) Prior Publication Data

US 2020/0237220 A1    Jul. 30, 2020

(30) Foreign Application Priority Data

Jan. 30, 2019 (JP) .................. 2019-014541

(51) Int. Cl.
*A61B 5/00* (2006.01)
*A61B 5/022* (2006.01)
*A61B 5/024* (2006.01)
*A61B 5/318* (2021.01)

(52) U.S. Cl.
CPC .......... *A61B 5/002* (2013.01); *A61B 5/02233* (2013.01); *A61B 5/024* (2013.01); *A61B 5/318* (2021.01)

(58) Field of Classification Search
CPC ..... A61B 5/002; A61B 5/02233; A61B 5/024; A61B 5/318
USPC ...................................................... 600/499
See application file for complete search history.

(56) References Cited

U.S. PATENT DOCUMENTS

| 2007/0194633 | A1* | 8/2007 | Ueda ................ | H04R 9/025 381/396 |
| 2013/0281868 | A1* | 10/2013 | Kawachi ............ | A61B 5/14552 600/485 |
| 2014/0114201 | A1* | 4/2014 | Watanabe ............ | A61B 5/6898 455/556.1 |
| 2016/0337757 | A1* | 11/2016 | Ozasa ................ | H04R 7/18 |
| 2018/0272147 | A1* | 9/2018 | Freeman ............... | G16H 50/30 |
| 2020/0229765 | A1* | 7/2020 | Peabody .............. | A61B 5/6824 |

FOREIGN PATENT DOCUMENTS

| JP | 5931855 B2 | 6/2016 | |
| WO | WO-2011156374 A2 * | 12/2011 | ........... A61B 5/0205 |

* cited by examiner

*Primary Examiner* — Alex M Valvis
*Assistant Examiner* — Chanel J Jhin
(74) *Attorney, Agent, or Firm* — Oliff PLC

(57) ABSTRACT

A biological information measurement device that performs sound wave communications with an external terminal including a microphone includes a housing; a measurement circuit that measures biological information; a modulation circuit that converts the biological information measured into a sound wave signal; and a vibration member that vibrates based on the sound wave signal transmitted from the modulation circuit. The measurement circuit, the modulation circuit and the vibration member are provided inside the housing. The housing includes a terminal placement surface on which the terminal is placed. The vibration member and the terminal placement surface are in contact with each other so that vibration of the vibration member is transmitted to the terminal placement surface.

8 Claims, 5 Drawing Sheets

BIOLOGICAL INFORMATION MEASUREMENT DEVICE

CROSS-REFERENCE TO RELATED APPLICATIONS

The present invention claims the priority of Japanese Patent Application No. 2019-014541 filed on Jan. 30, 2019, the entire content of which is hereby incorporated by reference.

TECHNICAL FIELD

The present invention relates to a biological information measurement device.

BACKGROUND ART

A device proposed in Patent Document 1 (Japanese Patent No. 5931855) acquires biological information of a subject, modulates the frequency of an electric signal indicating this biological information to convert this signal into a sound wave signal, and transmits sound waves based on this sound wave signal to an external terminal including a microphone. This device includes: a pair of electrodes that detect biological information, such as an electrocardiogram waveform, by being brought into contact with the body of a subject; a converter that modulates the frequency of the electrocardiogram waveform to convert the information into a sound wave signal; and an audio transmitter such as a speaker or a buzzer that transmits the sound waves to a terminal such as a smartphone. Upon receiving the sound waves, the smartphone can demodulate the sound wave signal to acquire the electrocardiogram waveform measured, and display it on a display for example.

However, a microphone of an external terminal such as a smartphone is usually arranged at an end of the terminal. Therefore, depending on the position and orientation of the terminal, the microphone may be unable to detect the sound transmitted from the speaker.

SUMMARY OF THE INVENTION

In view of this, an object of the present invention is to provide a biological information measurement device that communicates with an external terminal including a microphone to transmit sound waves, and enables the external terminal to detect the sound waves reliably regardless of the position and the orientation of the external device.

To achieve this object, a biological information measurement device that performs sound wave communications with an external terminal including a microphone according to an embodiment of the present disclosure includes:
a housing;
a measurement circuit that measures biological information;
a modulation circuit that converts the biological information measured into a sound wave signal; and
a vibration member that vibrates based on the sound wave signal transmitted from the modulation circuit, the measurement circuit, the modulation circuit and the vibration member being provided inside the housing, wherein
the housing includes a terminal placement surface on which the terminal is placed, and
the vibration member and the terminal placement surface are in contact with each other so that vibration of the vibration member is transmitted to the terminal placement surface.

BRIEF DESCRIPTION OF THE DRAWINGS

The present invention will become more fully understood from the detailed description given herein below and the accompanying drawings which are given by way of illustration only, and thus are not limitative of the presentation invention, and wherein.

EMBODIMENTS OF THE INVENTION

Hereinafter, an embodiment of an upper-arm sphygmomanometer as an example of a biological information measurement device according to the present invention will be described with reference to the accompanying drawings.

1: Upper-Arm Sphygmomanometer

Figure 1:
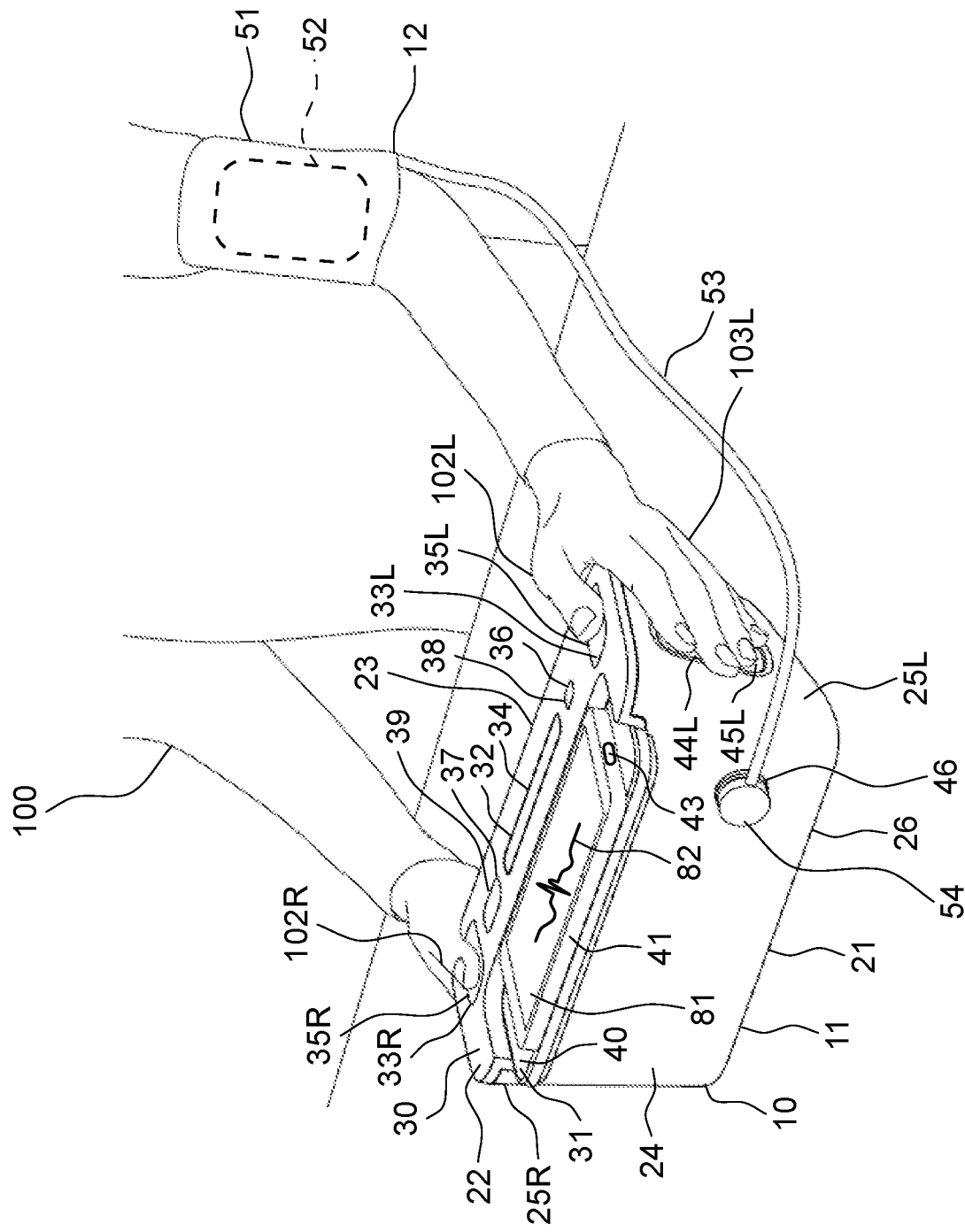
FIG. 1 is a schematic diagram illustrating a sphygmomanometer with an electrocardiogram waveform measurement function as a biological information measurement device according to an embodiment of the present invention.

FIG. 1 illustrates a schematic configuration of an upper-arm sphygmomanometer (hereinafter, appropriately referred to as a 'sphygmomanometer_) 10 according to an embodiment of the present invention. The sphygmomanometer 10 is a sphygmomanometer with an electrocardiogram waveform measurement function having a function of measuring the blood pressure and an electrocardiogram waveform of the subject 100.

2: Configuration of Upper-Arm Sphygmomanometer

As illustrated in FIG. 1, the sphygmomanometer 10 has a sphygmomanometer main body 11 and an arm cuff unit 12.

The sphygmomanometer main body 11 has a housing 21 incorporating various control devices to be described later. In the embodiment, the housing 21 has a box shape that is long in a lateral direction, and has an outer shape defined by an upper surface 22, a front surface 23, a back surface 24, left and right side surfaces 25 (25L, 25R), and a bottom surface 26.

In the embodiment, the upper surface 22 is inclined as a whole to have a height gradually increasing from the front surface 23 toward the back surface 24. A first interface region (man-machine interface region) 30 is disposed on the front surface 23 side. A second interface region (man-machine interface region) 31 is arranged on the back surface 24 side (see FIG. 2).

The first interface region 30 includes a display region 32 at the center in a left and right direction, and a pair of upper surface electrode regions 33 (33L and 33R) disposed on both sides of the display region 32 to be close to the left and right side surfaces 25 (25L and 25R). The central display region 32 has a laterally long rectangular shape, and has a display unit 34 arranged therein. Preferably, the display unit 34 is formed by a liquid crystal display. In the embodiment, the left and right upper surface electrode regions 33 have a vertically long rectangular shape that is long in a front and rear direction, and have reference electrodes 35 (35L and 35R) arranged therein. The reference electrode 35 has at least a surface formed of a conductive material, to be a portion the subject 100 touches with his/her body part (specifically, at least a right or left thumb 102 as illustrated in FIG. 1) when measuring the electrocardiogram waveform, to remove the noise that may otherwise be included in the electrocardiogram waveform.

The first interface region 30 includes, in addition to the display unit 34 and the reference electrodes 35, switch regions 36 and 37 that are respectively formed between the display unit 34 and the left electrode 35 and between the display unit 34 and the right electrode 35, and are respectively provided with a communication switch 38 and a start/stop switch 39.

In the embodiment, the second interface region 31 has a back surface side upper surface portion at a lower level than a front surface side upper surface portion provided with the first interface region 30. In the back surface side upper surface portion, a portable information terminal placement surface 40 that is flat and has a laterally long rectangular shape to be long in the left and right direction is formed. The portable information terminal placement surface 40 is a region where a portable information terminal 41 (for example, a smartphone) is placed. Therefore, the portable information terminal placement surface 40 is sized and shaped to be capable of stably supporting a commercially available portable information terminal of a normal size. In the embodiment, the portable information terminal placement surface 40 has a back end protruding backward from the back surface 24 of the housing 21 so as to be capable of supporting the entirety of the largest general portable information terminal available on the market. Furthermore, the surface of the portable information terminal placement surface 40 is inclined so as to have a height gradually increasing toward the back side.

As will be described later, the housing 21, and particularly the portable information terminal placement surface 40 is made of a material (polystyrene, acrylonitrile butadiene styrene, and acrylonitrile styrene, for example) with a sufficient hardness enabling the surface to vibrate as a whole in synchronization with the vibration of a vibration member 42 (see FIG. 2) that comes into contact with the back of the portable information terminal placement surface 40 as described later. Thus, the portable information terminal placement surface 40 entirely vibrates like a diaphragm of a speaker based on the vibration of the vibration member 42, so that sound waves can be oscillated toward the microphone 43 of the portable information terminal 41.

Both side surfaces 25 (25L, 25R) of the housing 21 have respective side electrode regions 44 (44L, 44R) that are provided with respective electrocardiogram waveform measurement electrodes 45 (a first electrocardiogram waveform measurement electrode 45L and a second electrocardiogram waveform measurement electrode 45R). The electrocardiogram waveform measurement electrodes 45 each have at least a surface formed of a conductive material, to be a portion the subject 100 touches with his/her body part (specifically, a finger 103 different from the thumb as illustrated in FIG. 1, such as an index finger, a middle finger, and a pinky) when measuring the electrocardiogram waveform.

As illustrated in FIG. 1, the back surface 24 of the housing 21 is provided with an arm cuff tube connection portion (connection hole for air supply) 46.

As illustrated in FIG. 1, the arm cuff unit 12 includes a belt-shaped arm cuff 51 incorporating an air bladder 52, and an air tube 53 having one end connected to the air bladder 52. At the other end of the air tube 53, a connector 54 shaped to be detachable is attached to the arm cuff tube connection portion 46 on the housing back surface 24. The connector 54 is connected to an end of a later described air supply circuit 55 (see FIG. 5) provided inside the housing 21. Therefore, the air bladder 52 is connected to the air supply circuit 55 (see FIG. 5) via the air tube 53 in a state where the connector 54 is connected to the arm cuff tube connection portion 46.

Figure 2:
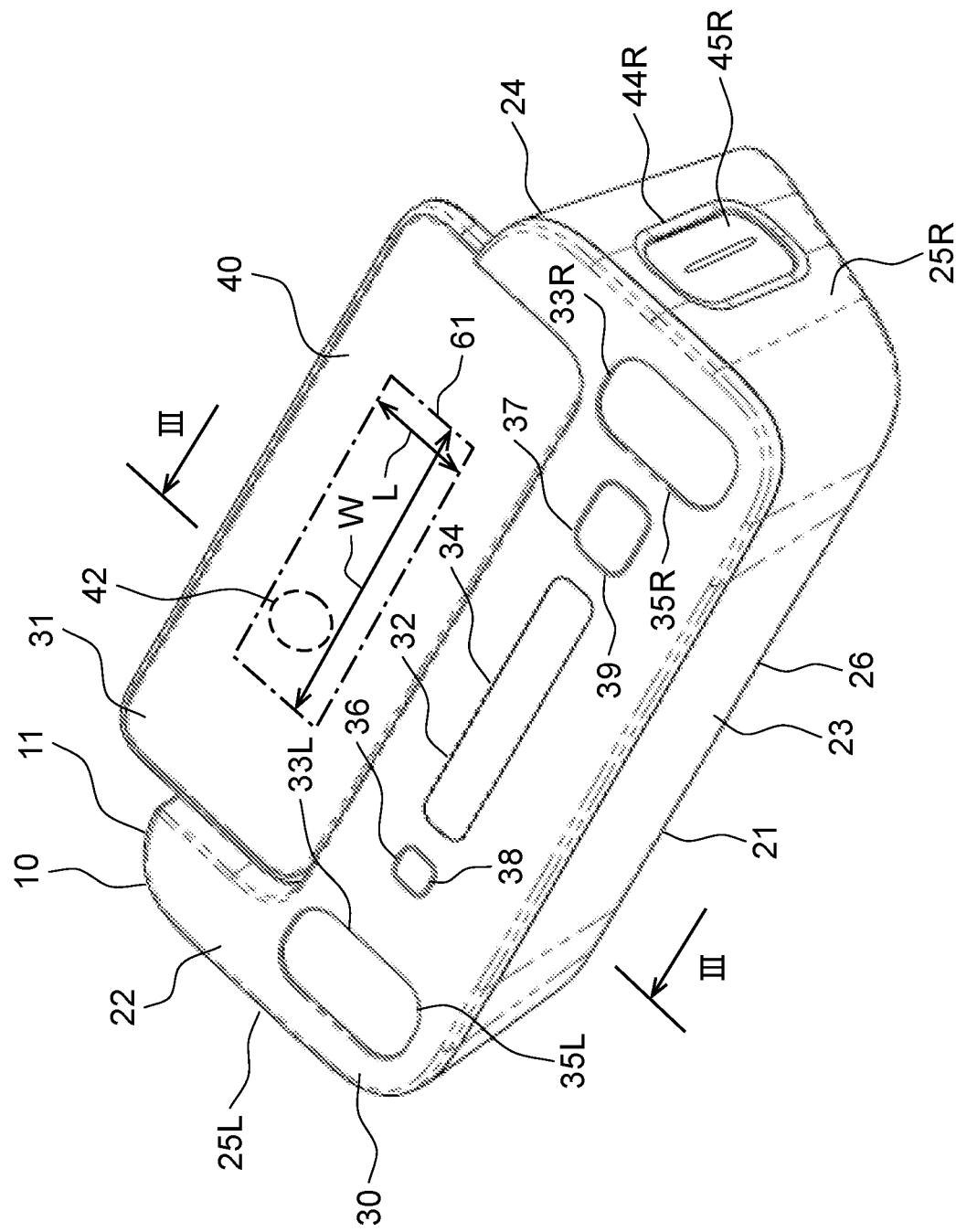
FIG. 2 is a perspective view of the sphygmomanometer illustrated in FIG. 1 as viewed from obliquely above.

As illustrated in FIG. 2, a piezoelectric diaphragm forming the vibration member 42 is disposed on the back surface side of the portable information terminal placement surface 40. The piezoelectric diaphragm 42 is arranged within a region 61 indicated by a one-dotted chain line. Preferably, the region 61 has a width W (=approximately 100 mm) between positions that are 50 mm away from the center of the portable information terminal placement surface 40 toward both sides in the left and right direction, and a length L (=about 30 mm) between positions that are 15 mm away from the center of the portable information terminal placement surface 40 toward both sides in the front and rear direction.

Figure 3:
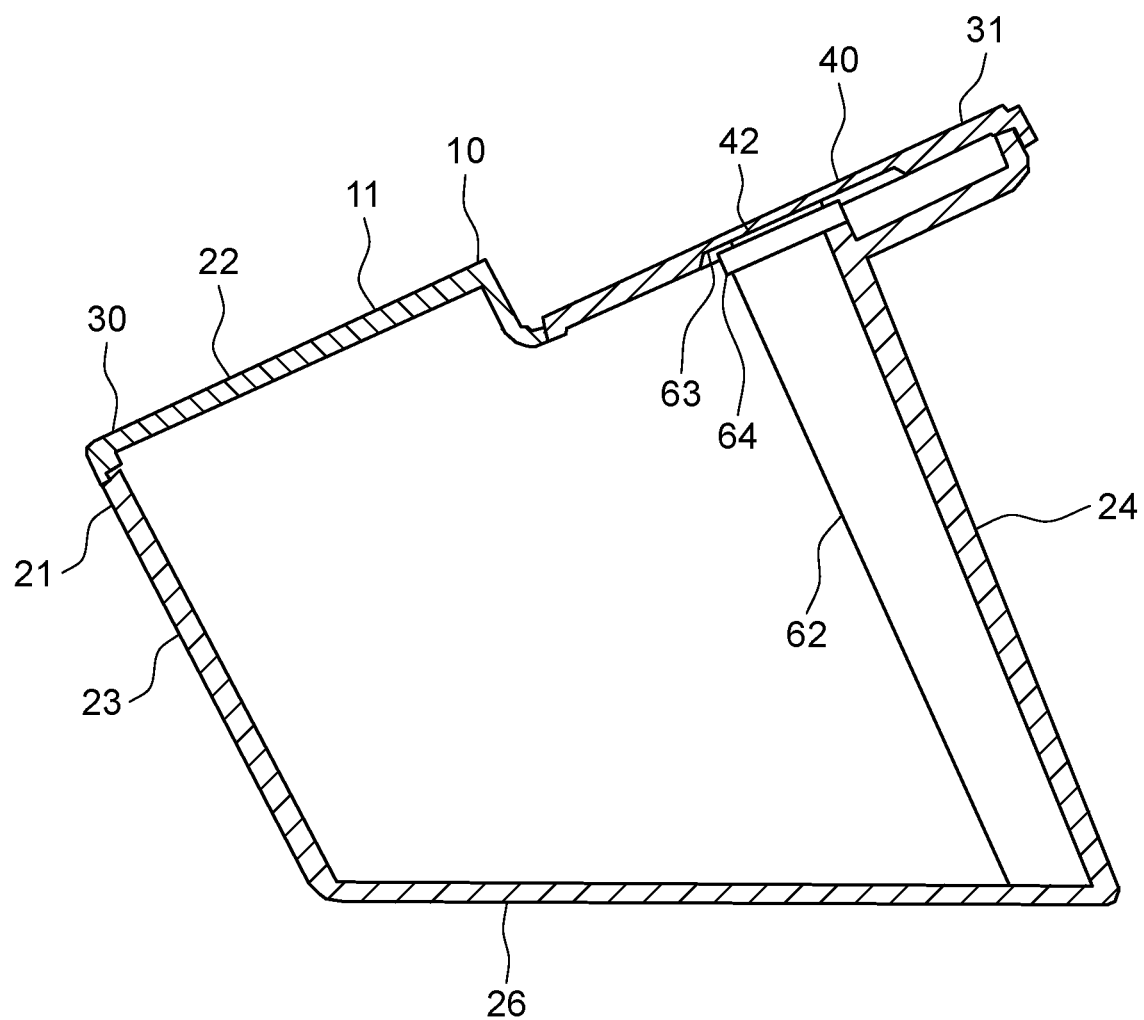
FIG. 3 is a cross-sectional view of the sphygmomanometer illustrating a position of a piezoelectric diaphragm, which is a vibration member, taken along a line III in FIG. 2.

As illustrated in FIG. 3, the piezoelectric diaphragm 42 is supported by the upper end of a rib 62 (supporting portion) provided inside the housing 21 and extending in an upper and lower direction along the housing back surface 24. In the embodiment, the portable information terminal placement surface 40 has a recess 63 formed in a lower surface region portion facing the upper end of the rib 62 and the piezoelectric diaphragm 42 supported by the upper end of the rib 62, with the thickness of this portion of this region reduced.

Figure 4:
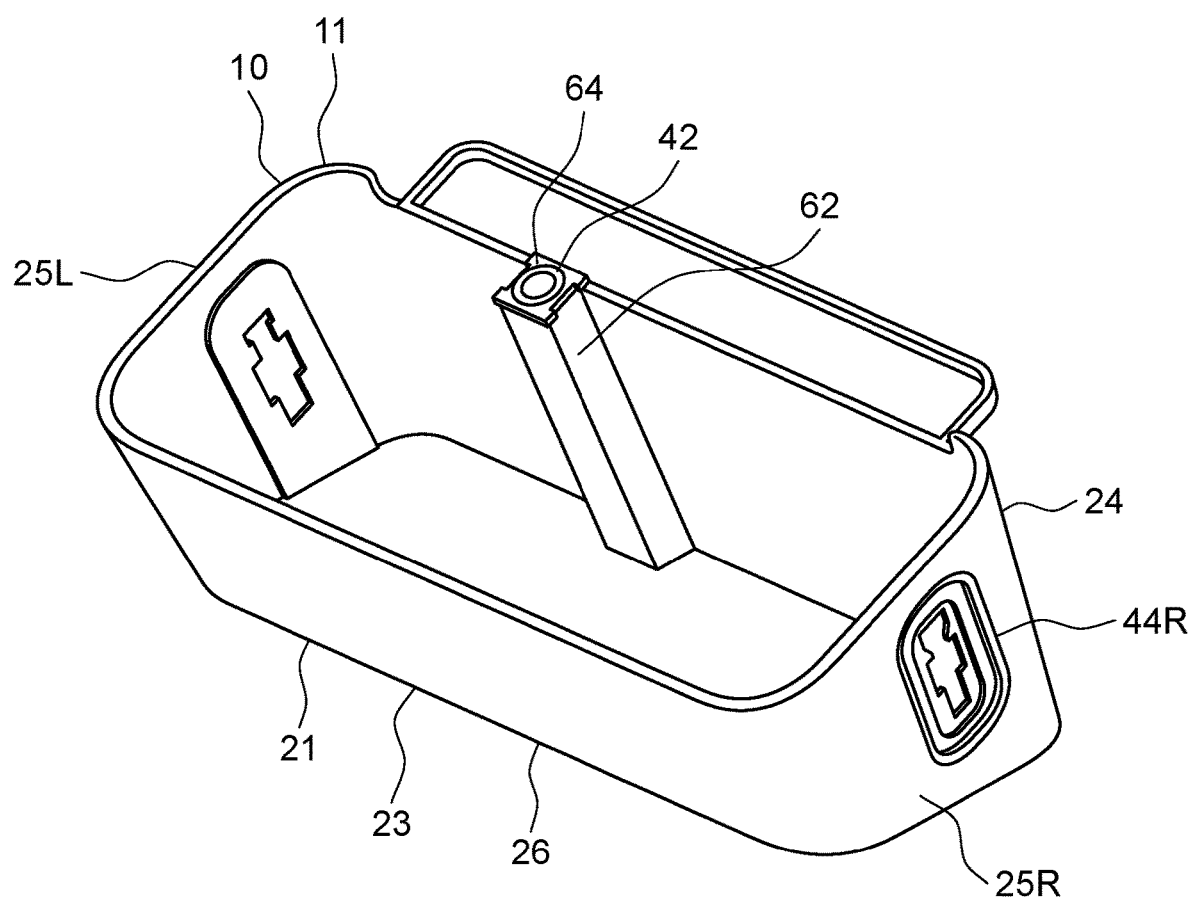
FIG. 4 is a perspective view illustrating the inside of a housing illustrated in FIG. 2.

As illustrated in FIG. 4, in the embodiment, the piezoelectric diaphragm 42 is arranged with an elastic member 64 provided between the rib 62 and the piezoelectric diaphragm 42. Thus, the piezoelectric diaphragm 42 is pressed against the portable information terminal placement surface 40 by the elastic restoration force of the elastic member 64.

Therefore, the vibration of the piezoelectric diaphragm 42 is reliably transmitted to the portable information terminal placement surface 40. Furthermore, the portion of the region corresponding to the lower surface of the recess 63 (see FIG. 3) that is in contact with the piezoelectric diaphragm 42 is thinner than other parts of the region. Thus, the vibration of the piezoelectric diaphragm 42 is transmitted to the portable information terminal 40 without largely attenuating.

Figure 5:
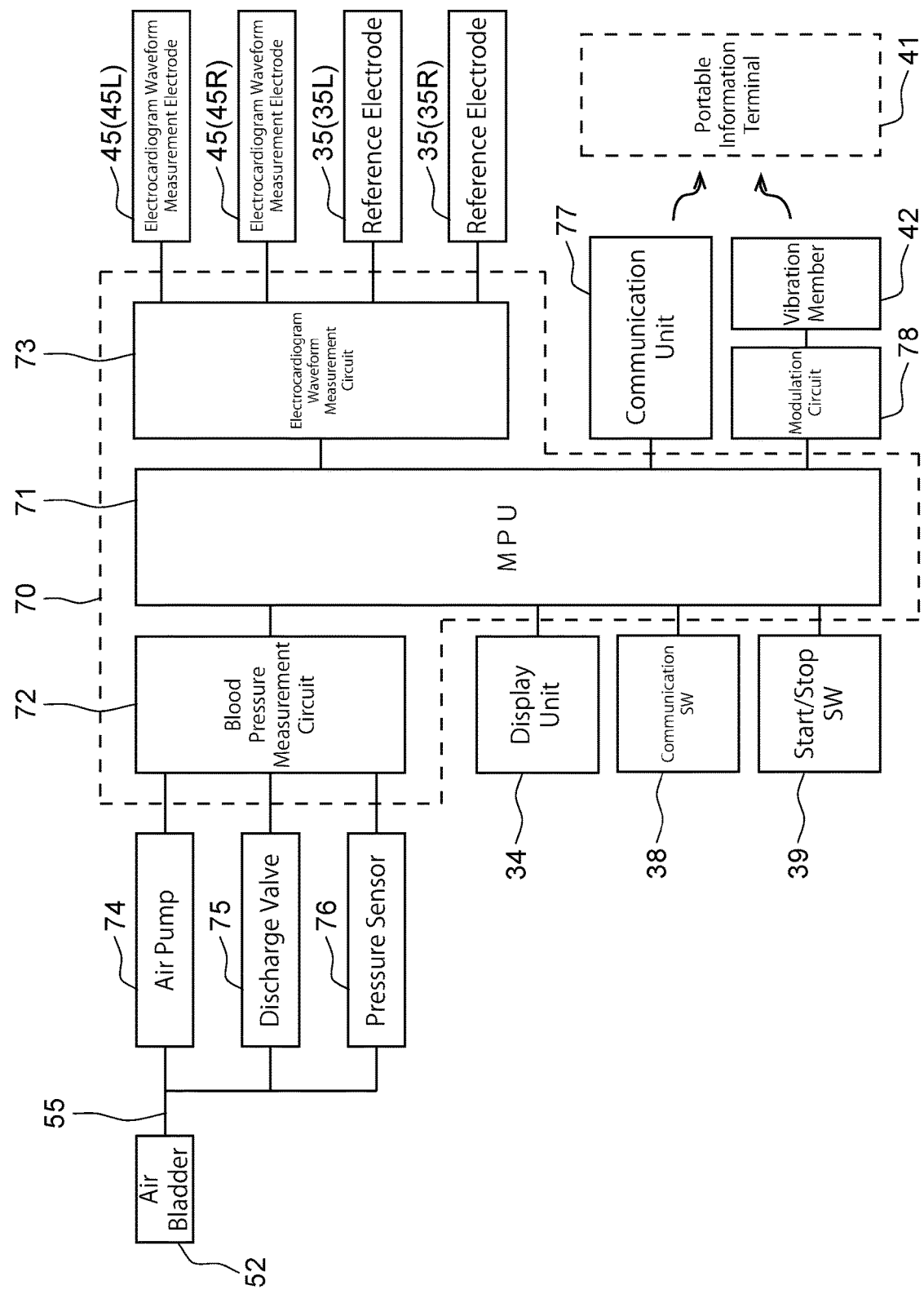
FIG. 5 is a control block diagram of the sphygmomanometer illustrated in FIG. 1.

The housing 21 incorporates a control unit 70 illustrated in FIG. 5. In the embodiment, the control unit 70 includes a processor 71 as well as a blood pressure measurement circuit 72 and an electrocardiogram waveform measuring circuit 73 that are connected to the processor 71 and are respectively communicably connected to a device related to blood pressure measurement, and a device related to electrocardiogram waveform measurement.

The device related to the measurement of blood pressure includes an air pump 74 that supplies air to the air bladder 52 of the arm cuff unit 12 via the air supply circuit 55, a discharge valve 75 for opening the air supply circuit 55 to the atmosphere to discharge the air from the air bladder 52, and a pressure sensor 76 that detects the pressure in the air supply circuit 55.

The device related to the measurement of the electrocardiogram waveform includes the above-described electrocardiogram waveform measurement electrodes 45 (the first electrocardiogram waveform measurement electrode 45L and the second electrocardiogram waveform measurement electrode 45R) and the reference electrodes 35 (35L and 35R).

The processor 71 is electrically connected to the display unit 34, the communication switch 38, and the start/stop switch 39. The processor 71 is configured to output a necessary signal to the display unit 34 in accordance with display contents to be displayed on the display unit 34, and when the communication switch 38 and the start/stop switch 39 are pressed, receive the corresponding signal from each of the communication switch 38 and the start/stop switch 39.

The processor 71 is also electrically connected to a communication unit 77 that wirelessly transmits the blood pressure and the pulse rate measured by the blood pressure measurement circuit 72, and is configured to wirelessly transmit the blood pressure and the pulse rate through the communication unit 77.

The processor 71 is further electrically connected to a modulation circuit 78 that converts the electrocardiogram waveform measured by the electrocardiogram waveform measurement circuit 73 into an ultrasound signal of 17 to 20 kHz which is less likely to be affected by disturbance such as noise. The modulation circuit 78 is electrically connected to the piezoelectric diaphragm 42 that vibrates based on the ultrasound signal. Thus, the processor 71 can output an electrocardiogram waveform in a form of an ultrasound wave through the modulation circuit 78 and the piezoelectric diaphragm 42.

When measuring blood pressure using the sphygmomanometer 10 configured as described above, as illustrated in FIG. 1, the connector 54 of the arm cuff unit 12 is connected to the arm cuff tube connection portion 46 of the housing 21, and the air bladder 52 is connected to the air supply circuit 55. In addition, the arm cuff 51 of the arm cuff unit 12 is wound around the upper arm of the subject 100. In this state, when the subject 100 presses (turns ON) the blood pressure measurement start/stop switch 39 on the housing upper surface 22, blood pressure measurement starts.

When the blood pressure measurement start/stop switch 39 is pressed (ON), a pressed (ON) signal is detected by the processor 71. When the processor 71 detects the pressed (ON) signal, in response to the signal, the blood pressure measurement circuit 72 drives the air pump 74 to supply air to the air bladder 52 through the air supply circuit 55, so that the upper arm of the subject 100 is compressed by the arm cuff 51. While air is being supplied to the air bladder 52 by the air pump 74, the pressure of the air bladder 52 (this corresponds to the pressure of the air supply circuit 55) is detected by the pressure sensor 76.

When it is detected from the output of the pressure sensor 76 that the pressure of the air bladder 52 has reached a predetermined pressure, the blood pressure measurement circuit 72 opens the discharge valve 75 to discharge the air in the air bladder 52. While the air is being discharged from the air bladder 52, the pressure of the air bladder 52 is detected by the pressure sensor 76.

The output of the pressure sensor 76 is detected by the blood pressure measurement circuit 72. The blood pressure measurement circuit 72 calculates the blood pressure (systolic blood pressure, diastolic blood pressure) and the pulse rate from the output of the pressure sensor 76 based on a predetermined blood pressure calculation algorithm, and outputs the calculation result to the processor 71. The processor 71 outputs and displays the blood pressure and the pulse rate received from the blood pressure measurement circuit 72 to and on the display unit 34.

After the blood pressure measurement, when the communication switch 38 on the housing upper surface 22 is pressed (turned ON), the blood pressure measurement circuit 72 transmits the blood pressure and the pulse rate to the portable information terminal 41 through the communication unit 77.

When an electrocardiogram waveform is measured, the portable information terminal 41 is placed on the portable information terminal placement surface 40 as illustrated in FIG. 1. Dedicated software (application) for receiving the electrocardiogram waveform information output from the sphygmomanometer 10 by the portable information terminal 41 and displaying the received electrocardiogram waveform information on the display of the portable information terminal 41 is installed in the portable information terminal 41. In this state, the subject 100 touches the electrocardiogram waveform measurement electrodes 45 on the left and right sides with his/her fingers 103 (index finger, middle finger, or ring finger) other than the left and right thumbs. The subject 100 also touches the reference electrode(s) 35 on the upper surface 22 with one of the left and right thumbs 102 or both.

When the subject 100 touches the electrocardiogram waveform measurement electrodes 45 with the fingers 103 of both hands, the electrocardiogram waveform measurement circuit 73 detects that the electrocardiogram waveform measurement electrodes 45 are electrically brought into contact with each other through the subject 100, and is triggered by this detection signal to start the electrocardiogram waveform measurement. In this state, the thumb(s) 102 of one of left and right hands of the subject 100 or both is in contact with the reference electrode(s) 35.

In this state, there is a potential difference between the signal input to the reference electrode 35 and the signal input to the electrocardiogram waveform measurement electrode 45. This potential difference is caused by a difference in length between paths to the thumb 102 and the other finger 103. The signals input to the reference electrode 35 and to the electrocardiogram waveform measurement electrode 45 include noise at substantially the same level. Thus, an electrocardiogram waveform less affected by noise can be obtained by measuring potential difference between the signals input to the reference electrode 35 through the thumb 102 and to the electrocardiogram waveform measurement electrode 45 through the other finger 103, and amplifying the potential difference as appropriate.

The measured electrocardiogram waveform is converted into an ultrasound signal by the modulation circuit 78, and then is transmitted directly to the portable information terminal placement surface 40 through the vibration of the piezoelectric diaphragm 42. In this process, the entire portable information terminal placement surface 40 functions as a speaker diaphragm, and emits ultrasound waves corresponding to the measured electrocardiogram waveform. Therefore, in any of the cases where the portable information terminal 41 is placed on the portable information terminal placement surface 40 with the microphone 43 directed right or left, or where the portable information terminal 41 is placed with the microphone 43 and the portable information terminal placement surface 40 disposed close to each other, the microphone 43 reliably detects the sound waves from the portable information terminal placement surface 40.

The portable information terminal 41 that has received an electrocardiogram waveform 82 displays it on a display 81 of the portable information terminal 41 in real time in accordance with the installed software. The electrocardiogram waveform information is stored in a memory of the portable information terminal 41 together with other measurement information (measurement date and time). The electrocardiogram waveform information stored in the memory can be transmitted to another communication terminal if needed.

Thus, according to the sphygmomanometer 10 and the sphygmomanometer main body 11 according to the above-described embodiment, the microphone 43 of the portable information terminal 41 is always near the diaphragm (sound wave source) while being placed on the portable information terminal placement surface 40. Therefore, regardless of the orientation of the portable information terminal 41, the microphone 43 of the portable information terminal 41 can reliably receive the sound wave emitted from the portable information terminal placement surface 40.

3: Other Embodiments

Although the embodiment of the sphygmomanometer has been described as an example of the biological information measurement device according to the present invention, the biological information measurement device can be modified in various ways to be other embodiments.

For example, in the above-described embodiment, a sphygmomanometer with an electrocardiogram waveform measurement function is proposed as a biological information measurement device. Alternatively, the biological information measurement device may be a physical strength measurement device such as a weight scale, a thermometer, a blood glucose meter, or a grip meter.

Furthermore, in the above-described embodiment, the electrocardiogram waveform is converted into an ultrasound signal. Alternatively, the electrocardiogram waveform may be converted into a sound wave signal having a frequency from 20 Hz to 16 kHz, which is generally audible to a subject. In this case, the biological information measurement device may be provided with a magnetic sounder that generates sound waves based on a change in magnetic flux density, instead of the piezoelectric diaphragm 42. The standard frequency of sound waves that a general magnetic sounder can oscillate is about 1 to 4 kHz and thus, sound waves audible to the subject is emitted.

In the above embodiment, the portable information terminal 41 may be a smartphone or a tablet terminal including a microphone. It is preferable that the size of the portable information terminal placement surface 40 be appropriately designed in accordance with the expected size of the terminal.

The portable information terminal 41 may be placed on the portable information terminal placement surface 40 via a case attached to the portable information terminal 41. As long as the microphone of the portable information terminal 41 is arranged in the vicinity of the portable information terminal placement surface 40, the ultrasound wave communication is sufficiently performed even if the smartphone itself is separated from the portable information terminal placement surface 40.

As described above, a biological information measurement device that performs sound wave communications with an external terminal including a microphone according to an embodiment of the present disclosure includes:
a housing;
a measurement circuit that measures biological information;
a modulation circuit that converts the biological information measured into a sound wave signal; and
a vibration member that vibrates based on the sound wave signal transmitted from the modulation circuit, the measurement circuit, the modulation circuit and the vibration member being provided inside the housing, wherein
the housing includes a terminal placement surface on which the terminal is placed, and
the vibration member and the terminal placement surface are in contact with each other so that vibration of the vibration member is transmitted to the terminal placement surface.

With this biological information measurement device, the entire terminal placement surface can oscillate to emit the sound waves indicating the measured biological information. Therefore, by arranging the microphone of the external terminal near the terminal placement surface, the measured biological information can be reliably transmitted to the external terminal regardless of the orientation of the external terminal itself.

The biological information measurement device according to another embodiment further includes:
a supporting portion fixed to the housing; and
an elastic member provided between the supporting portion and the vibration member, wherein
the vibration member is pressed against the terminal placement surface by the elastic member.

With this biological information measurement device, the vibration member and the terminal placement surface can be in contact with each other with no gap in between, so that the entire terminal placement surface can reliably oscillate to emit the sound waves indicating the measured biological information.

In the biological information measurement device according another embodiment, the vibration member is a piezoelectric diaphragm.

With this biological information measurement device, a high frequency sound waves, for example, ultrasound waves can be oscillated from the entire terminal placement surface, so that the measured biological information can be reliably transmitted to the portable information terminal.

In the biological information measurement device according to another embodiment, the sound wave signal is an ultrasound signal at a frequency from 17 to 20 kHz.

With the biological information measurement device, the frequency of the ultrasound waves emitted from the entire terminal placement surface is set to be within a band detectable by a microphone of an external terminal such as a general portable information terminal (for example, a smartphone) available on market, so that the biological information measured can be transmitted to general external terminals.

In the biological information measurement device according to another embodiment,
the terminal placement surface has a width in a left and right direction being longer than a length of the terminal placement surface in a front and rear direction,
the width is at least 100 mm,
the length is at least 30 mm, and the vibration member is provided in a region of 15 mm toward each side in the front and rear direction from center of the terminal placement surface and 50 mm toward each side in the left and right direction from the center.

With this biological information measurement device, an external terminal such as a general portable information terminal available on the market may be placed on the terminal placement surface. Furthermore, even if the microphone of the external terminal is at the end of the terminal placement surface, the measured biological information can be reliably transmitted to the external terminal.

In the biological information measurement device according to another embodiment,
the measurement circuit includes an electrocardiogram waveform measurement circuit that measures an electrocardiogram waveform of a subject,
the housing has an outer surface provided with a first electrocardiogram waveform measurement electrode and a second electrocardiogram waveform measurement electrode electrically connected to the electrocardiogram waveform measurement circuit, and
the modulation circuit converts the electrocardiogram waveform measured by the electrocardiogram waveform measurement circuit into the sound wave signal.

With this biological information measurement device, the electrocardiogram waveform measurement is performed with the subject's hand touching the first electrocardiogram waveform measurement electrode and the second electrocardiogram waveform measurement electrode, and the entire terminal placement surface can oscillate sound waves indicating the measured electrocardiogram waveform.

In the biological information measurement device according to another embodiment,
the biological information measurement device forms a part of an upper-arm sphygmomanometer that measures blood pressure of a subject, and
the housing accommodates
an air supply circuit that supplies air to an air bladder accommodated in an arm cuff of the upper-arm sphygmomanometer,
an air pump that supplies air to the air bladder through the air supply circuit,
a pressure sensor that detects pressure of air in the air supply circuit, and
a blood pressure measurement circuit that measures the blood pressure of the subject based on an output from the pressure sensor.

With this biological information measurement device, the electrocardiogram waveform measurement and the blood pressure measurement can be performed at once with the arm cuff connected to the air supply circuit.

The biological information measurement device according to another embodiment further includes an arm cuff unit, and
the arm cuff unit includes
a belt-shaped arm cuff incorporating an air bladder, and
an air tube that has one end connected to the air bladder, and supplies air to the air bladder,
the biological information measurement device further comprises a tube connection portion to which another end of the air tube is detachably connected, the tube connection portion being provided on a surface of the housing, and
the tube connection portion is connected to the air supply circuit.

With this biological information measurement device, the electrocardiogram waveform measurement and the blood pressure measurement can be performed at once.

According to the invention of the present application, the entire terminal placement surface oscillates the sound waves indicating the measured biological information, so that the microphone of the external terminal can reliably detect the sound waves regardless of the set position or orientation of the microphone of the external terminal.

It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:
1. A biological information measurement device configured so as to perform sound wave communications with an external terminal including a microphone, the biological information measurement device comprising:
a housing comprising:
a bottom surface,
an upper surface positioned opposite to the bottom surface, with an interior space present between the bottom surface and the upper surface,
a front surface extending from the bottom surface to the upper surface on a front side of the housing,
a back surface extending from the bottom surface to the upper surface on a back side of the housing, and
a first side surface and a second side surface extending from the bottom surface to the upper surface on left and right sides of the housing, wherein
the interior space of the housing is bounded by the upper surface, the bottom surface, the front surface, the back surface, the first side surface, and the second side surface,
the biological information measurement device further comprising:
a measurement circuit that measures biological information;
a modulation circuit that converts the biological information measured into a sound wave signal; and
a vibration member that vibrates based on the sound wave signal transmitted from the modulation circuit, wherein
the measurement circuit, the modulation circuit and the vibration member are disposed within the interior space of the housing,
the housing includes, as a portion of the upper surface, a terminal placement surface extending flatly,
the terminal placement surface having a predetermined size and shape for the external terminal including the microphone to be placed,
a specific region of the terminal mounting surface is disposed inwardly with respect to a peripheral region of the terminal placement surface and includes a center of the terminal mounting surface, the specific region having a first width in a left and right direction and a first length in a front and back direction,
the vibration member has a plate shape arranged along the terminal mounting surface, a second width and a second length of the vibration member along the terminal placement surface being smaller than the first width and the first length of the specific region of the terminal placement surface, respectively, an elastic member is provided in the interior space of the housing in a state where the elastic member contacts an entire lower surface of the vibration member, the entire lower surface of the vibration member is pressed by the elastic member upwardly, such that an entire upper surface of the vibration member is pressed against the specific region of the terminal mounting surface upwardly from the interior space of the housing, and when transmitting the sound wave signal, vibration of the vibration member based on the sound wave signal is transmitted from the vibration member upwardly to the specific region of the terminal placement surface to vibrate from the specific region an entirety of the terminal placement surface, and then the vibration is output from the entirety of the terminal placement surface as the sound wave signal.

2. The biological information measurement device according to claim 1 further comprising:

a supporting portion fixed to a position in the interior space of the housing, the position being downward with respect to the vibration member, wherein the elastic member is arranged in a space between the supporting portion and the vibration member, and the vibration member is pressed upwardly against the terminal placement surface by an elastic restoration force of the elastic member.

3. The biological information measurement device according to claim 1, wherein the vibration member is a piezoelectric diaphragm.

4. The biological information measurement device according to claim 1, wherein the sound wave signal is an ultrasound signal at a frequency from 17 to 20 kHz.

5. The biological information measurement device according to claim 1, wherein the first width of the specific region is 50 mm toward each side in the left and right direction from the center of the terminal placement surface, and the first length of the specific region is 15 mm toward each side in the front and back direction from the center of the terminal placement surface.

6. The biological information measurement device according to claim 1, wherein the measurement circuit includes an electrocardiogram waveform measurement circuit that measures an electrocardiogram waveform of a subject, the first side surface and the second side surface of the housing are respectively provided with a first electrocardiogram waveform measurement electrode and a second electrocardiogram waveform measurement electrode electrically connected to the electrocardiogram waveform measurement circuit, and the modulation circuit converts the electrocardiogram waveform measured by the electrocardiogram waveform measurement circuit into the sound wave signal.

7. The biological information measurement device according to claim 1, wherein the biological information measurement device forms a part of an upper-arm sphygmomanometer that measures blood pressure of a subject, and the housing accommodates, within the interior space, an air supply circuit that supplies air to an air bladder accommodated in an arm cuff of the upper-arm sphygmomanometer, an air pump that supplies air to the air bladder through the air supply circuit, a pressure sensor that detects pressure of air in the air supply circuit, and a blood pressure measurement circuit that measures the blood pressure of the subject based on an output from the pressure sensor.

8. The biological information measurement device according to claim 7 further comprising:

an arm cuff unit that includes the arm cuff and an air tube having one end connected to the air bladder of the arm cuff, for supplying air to the air bladder, and a tube connection portion to which another end of the air tube is detachably connected, the tube connection portion being provided on the back surface of the housing, and the tube connection portion is connected to the air supply circuit.

* * * * *